US00PP14629P39

(12) United States Plant Patent
Byrne et al.

(10) Patent No.: US PP14,629 P3
(45) Date of Patent: Mar. 23, 2004

(54) PEACH TREE NAMED 'TEXPRINCE'

(50) Latin Name: *Prunus persica*
Varietal Denomination: TexPrince

(75) Inventors: David Byrne, Bryan, TX (US); Terry Bacon, Bakersfield, CA (US)

(73) Assignee: The Texas A&M University System, College Station, TX (US)

( * ) Notice: Subject to any disclaimer, the term of this patent is extended or adjusted under 35 U.S.C. 154(b) by 36 days.

(21) Appl. No.: 10/114,413

(22) Filed: Apr. 2, 2002

(65) Prior Publication Data

US 2003/0188353 P1 Oct. 2, 2003

(51) Int. Cl.[7] ..... A01H 5/00

(52) U.S. Cl. ..... Plt./198

(58) Field of Search ..... Plt./198

*Primary Examiner*—Bruce R. Campell
*Assistant Examiner*—Susan B. McCormick
(74) *Attorney, Agent, or Firm*—Fulbright & Jaworski LLP

(57) ABSTRACT

A new and distinct variety of *Prunus persica* named 'TexPrince' is provided. This variety requires approximately 500 to 550 chilling units of dormancy and produces an attractively colored freestone peach that ripens in early midseason suitable for commercial production.

5 Drawing Sheets

Figure 1:
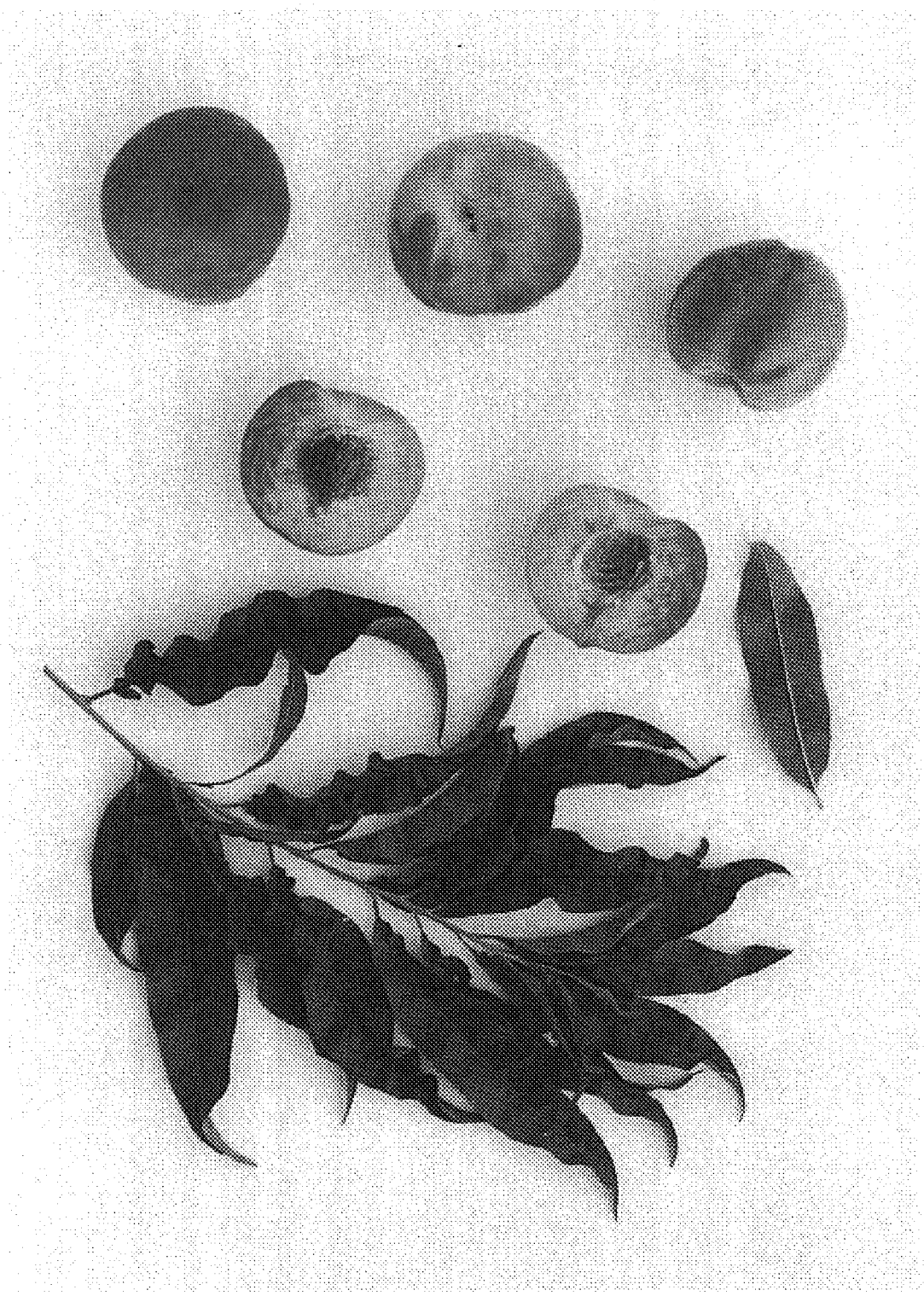

Variety denomination: Variety of *Prunus persica*, denominated as 'TexPrince'.

BACKGROUND OF THE INVENTION

The present invention relates to a new, novel and distinct variety of peach tree, which is denominated varietally as 'TexPrince'. The 'TexPrince' peach tree produces a high quality, firm freestone peach that matures early mid-season and requires approximately 500 to 550 chilling units of dormancy.

BRIEF SUMMARY OF THE INVENTION

The 'TexPrince' peach is characterized as to novelty and is otherwise noteworthy by producing fruit which ripens in the early midseason that is high quality, firm and has attractive coloration. In this regard, the present peach tree variety bears fruit that are ripe for commercial harvesting and shipment in early to middle June, when the fruit is grown in central Texas. This is comparable to or shortly after the peach tree varieties 'TexRoyal' (not patented) (Byrne and Bacon, 1991, *HortScience* 26:1338–1340) and 'Juneprince' (not patented) (Okie and Reilly, 1987, *HortScience* 22:325–326). Additionally, 'TexPrince' exhibits the potential to be commercialized in regions that have relatively low chilling requirements (i.e., 500 to 600 chilling units) or in regions having higher chilling requirements provided spring frosts do not occur.

ORIGIN OF THE VARIETY

The present peach tree was the result of an on going Stone Fruit Breeding Program of Texas A&M University, College Station, Tex. To this end, both controlled and hybrid crosses are made each year in order to produce seedling populations from which improved progenies are evaluated and selected.

The seedling 'TexPrince' originated at the Stone Fruit Breeding Program of the Department of Horticultural Sciences, Texas A&M University, located in College Station, Tex. In 1989, a controlled cross was made on selection P60-12 at the USDA, ARS Horticulture Fruit Crops Research Laboratory. The P60-12 selection is a selection from a cross between 'Firebrite' (ASHS, 1997, The Brooks and Olmo Register of Fruit and Nut Varieties) and 'Sunfre' (Ramming and Andrews, 1982, *HortScience* 17:412), and was pollinated with pollen from 'Flordaking', a non-patented variety released by the University of Florida (Andrews et al., 1979, *HortScience* 14:81–82).

Resulting seedlings from this cross were planted in a high-density fruiting nursery at College Station in 1990. In 1992, 'TexPrince' was marked for subsequent observation and noted as having exceptional characteristics, including mid-season maturity, large fruit size, good productivity, yellow ground color, round shape, high red overcolor, and excellent firmness. It was propagated asexually by budding and has been evaluated in Texas and California.

ASEXUAL REPRODUCTION

The new variety 'TexPrince' was bud grafted onto virus free 'Nemaguard' (not patented) (ASHS, 1997, The Brooks and Olmo Register of Fruit and Nut Varieties) peach rootstock in May, 1992. The budded trees of 'TexPrince' were planted at the experimental orchards at Texas A&M University near the city of College Station, Tex., County of Brazos and near the city of Yoakum, Tex., County of Dewitt. Additionally, the trees were planted at the experimental orchards near the city of Fowler, Calif., County of Fresno, in the central portion of the San Joaquin Valley of California. Fruit from the resulting propagation has been evaluated for the 1995 to 2001 fruit seasons in College Station and in Yoakum, and for the 1998 to 2001 fruit seasons in Fowler. This evaluation clearly demonstrated that the re-propagated trees are true to the characteristics of the original seedling in all observable aspects.

BRIEF DESCRIPTION OF THE PHOTOGRAPHS

FIG. 1. is a color photograph of a characteristic twig bearing typical leaves; several leaves showing both the dorsal and ventral coloration, and several leaves showing their external coloration sufficiently matured for harvesting and shipment. Additionally, one fruit of the subject variety is dissected in the axial or suture plane to illustrate the flesh and stone characteristics thereof. These fruit were harvested Jun. 23, 2000 at the experimental plots in Fowler, Calif.

Figure 2:
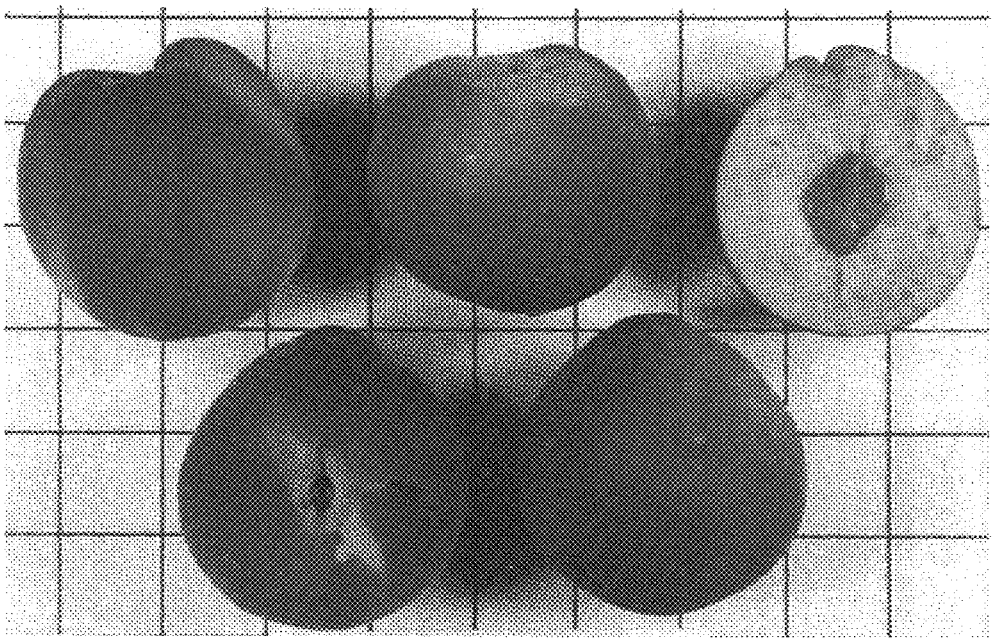

FIG. 2. is a color photograph of mature fruit of 'Tex-Prince' harvested from experimental orchards near College Station, Tex. on Jun. 7th, 1994. Whole fruit in four positions and a cross section of one fruit are presented to show the yellow flesh with red flecking.

Figure 3:
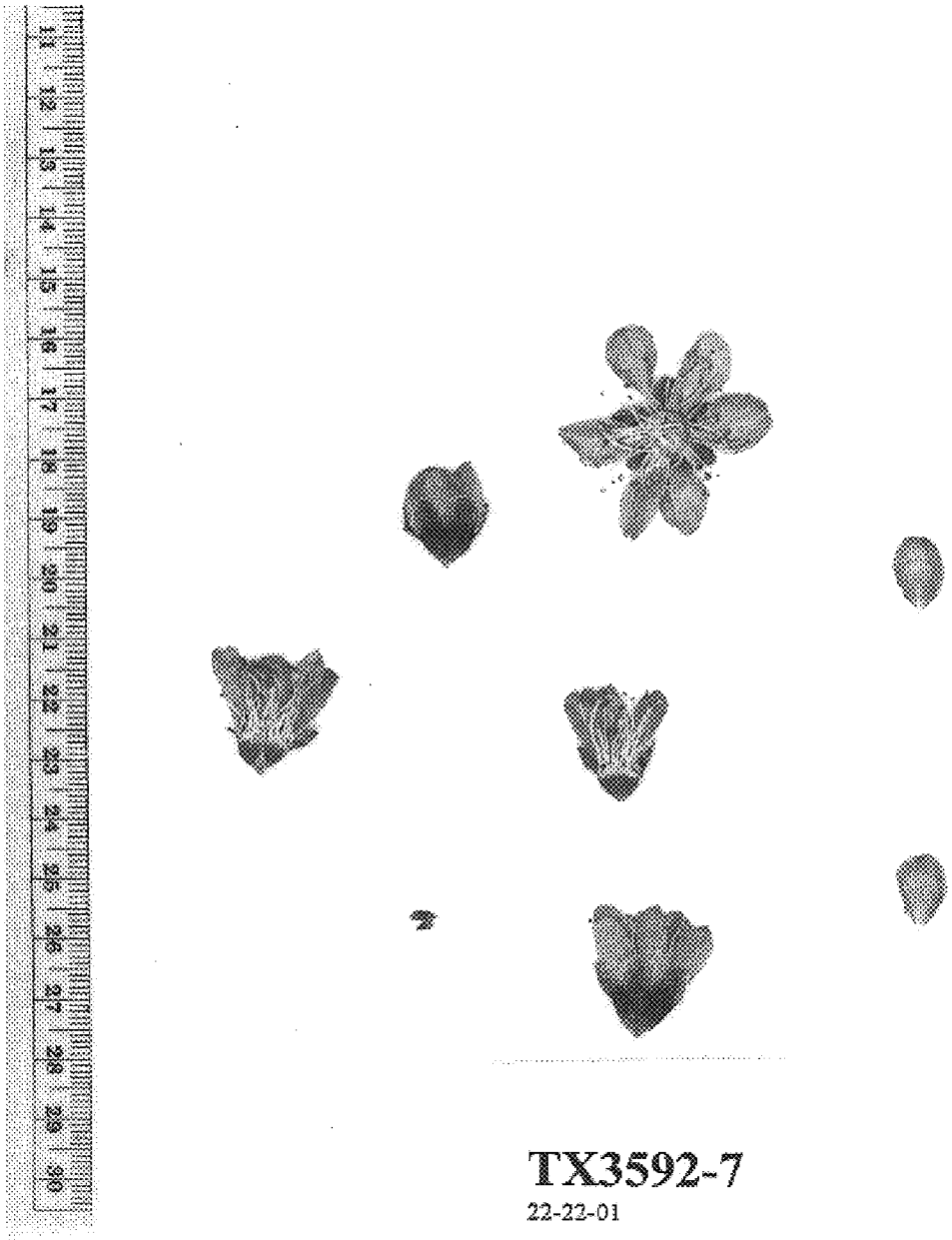

FIG. 3. illustrates the typical non-showy flowers of 'Tex-Prince' observed on trees propagated at experimental plots in College Station, Tex. on Feb. 22, 2001.

Figure 4:
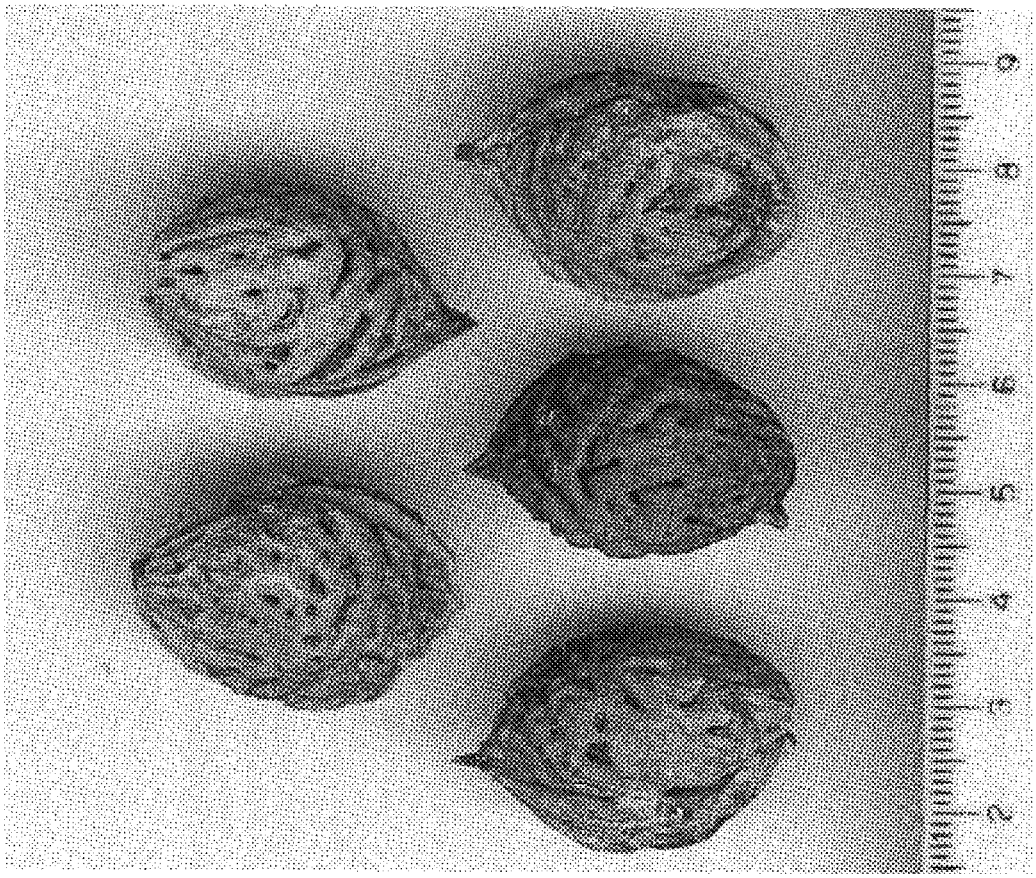

FIG. 4. illustrates the pits (endocarp) of 'TexPrince' fruit.

Figure 5:
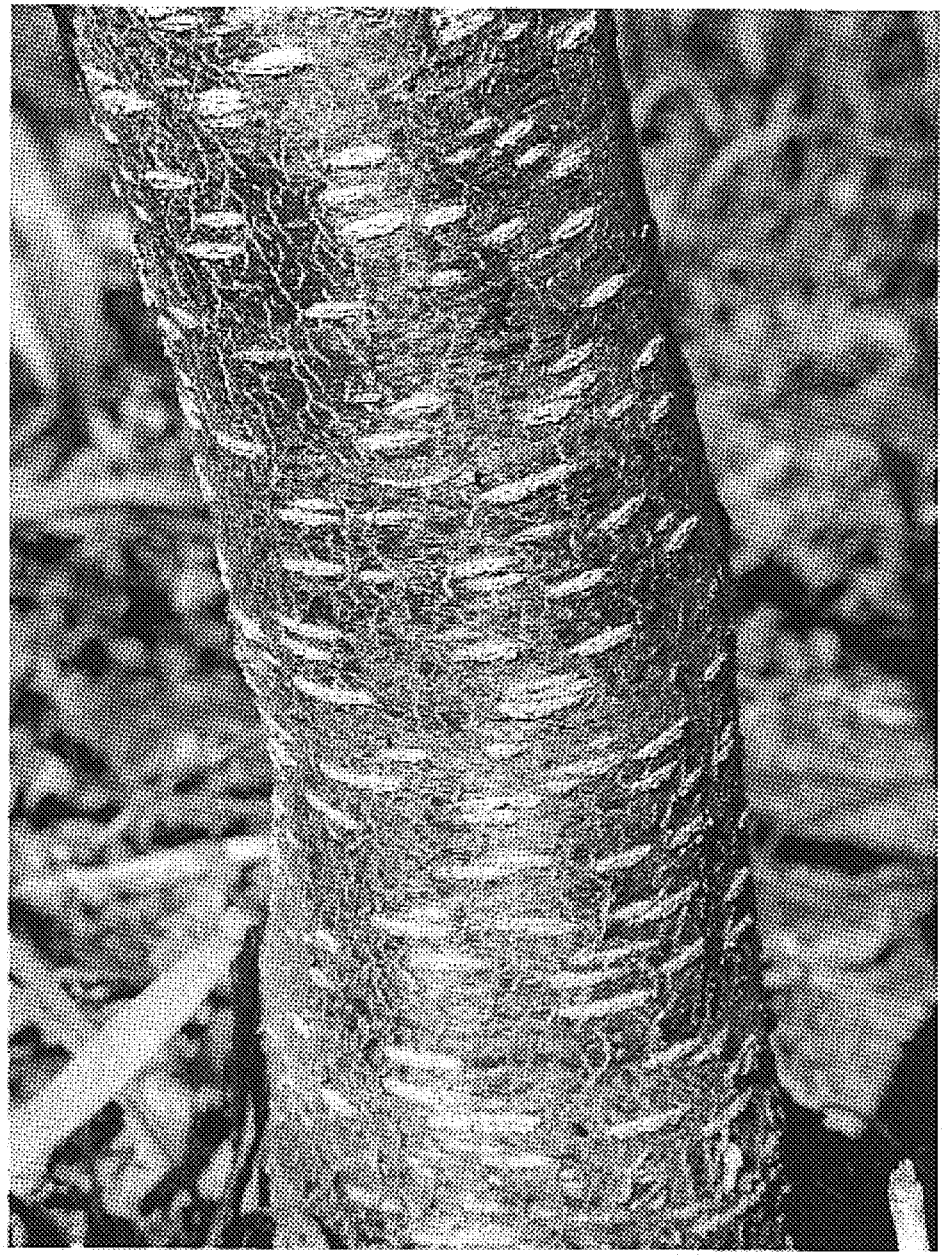

FIG. 5. illustrates that bark on the trunk of a third leaf 'TexPrince' tree. The diameter of the trunk is about 10 centimeters.

DETAILED BOTANICAL DESCRIPTION

Referring more specifically to the pomological details of this new and distinct variety of peach tree, the following has been observed under the ecological conditions prevailing at the experimental orchards near the town of Fowler, county of Fresno, state of California and of Texas A&M University, College Station, Brazos County, Tex. and Yoakum, DeWitt County, Tex. The color and size designations are from samples collected in the experimental orchards of Texas A&M University unless otherwise noted. All major color code designations are by reference to The R.H.S. Colour Chart (Third Edition) provided by The Royal Horticultural Society of Great Britain and descriptors are from the New Jersey Agricultural Experiment Station Bulletin 728 entitled, 'Standards for Classifying Peach Characters' by M. A. Blake and L. J. Edgerton published in 1946. Colors are approximate as color depends on horticultural practices such as, for example, light level and fertilization rate.

Tree:

*Size.*—Average or above average as compared to other common peach cultivars ripening in the early mid-season of maturity.

*Productivity.*—Productive. Normal fruit set is greater than is needed for a full crop and fruit thinning is required to obtain optimal marketable fruit size. The amount of fruit set will vary with the climatic conditions at bloom time.

*Growth form.*—The 'TexPrince' peach has been trained in central leader configuration in California and an open center in the Texas experimental orchards. Training and pruning methods of trees controls branch size and crotch angles. Thus the natural growth habit of the tree is not seen since poorly angled (narrow) or positioned branches are removed. When trained as an open center, it displays a semi-upright growth habit.

*Height.*—3 meters at the end of the third growing season.

*Width.*—2 meter tree width at the end of the third growing season as a 3rd leaf tree.

*Current season growth.*—The current season growth for the new variety was approximately 45 to 95 cm.

*Regularity of bearing.*—Regular and considered hardy under typical central San Joaquin Valley (Fowler, Calif.) and south central Texas (College Station and Yoakum) conditions.

*Pollination requirements.*—This tree is self-fertile.

Trunk:

*Thickness.*—Approximately 9.5 cm in diameter when measured at a distance of approximately 30 cm above the soil level, at the end of the 2001 growing season on trees at the end of the third growing season.

*Bark texture.*—Considered moderately rough.

*Lenticels.*—Numerous flat, oval lenticels present. The lenticels range in size in size from approximately 4 to 25 millimeters in width and from 1 to 2 millimeters in height.

*Bark coloration.*—Variable, but it is generally considered to be a grey-brown (RHS Black Group 202D).

Branches:

*Size.*—Considered medium for the variety.

*Surface texture.*—Average.

*Thickness.*—The average branch diameter is 4.9 cm.

*Current season shoots.*—Surface texture — Substantially glabrous.

*Internode length.*—Approximately 1.7 to 2.3 cm.

*Color of mature branches.*—Medium brown, (RHS Grey Brown Group 199A to the Brown Group 200D).

*Current seasons shoots.*—Color — Light green, (RHS Yellow Green Group 143C).

Leaves:

*Size.*—Considered moderately large for the species. Leaf measurements have been taken from vigorous upright current season growth approximately at mid-shoot.

*Leaf length.*—Approximately 220 to 250 millimeters.

*Leaf width.*—Approximately 36 to 48 millimeters.

*Leaf form.*—Lanceolate.

*Leaf tip form.*—Sharply acute. The tip often appears flexed downwards and slightly twisted laterally.

*Leaf color.*—Dark green (RHS Green Group 137A).

*Lower surface.*—Green (RHS Green Group 137C).

*Mid-vein.*—Color — Light yellow green (RHS Yellow Green Group 144C).

*Leaf margins.*—Form — Considered crenate. Uniformity — Considered generally uniform.

*Leaf petioles.*—Size — Considered medium long. Length — Approximately 12 to 15 mm. Thickness — Approximately 1.5 to 2 mm. Color — Pale green, (RHS Yellow Green Group 146B).

*Leaf glands.*—Size — Medium, approximately 2–3 mm in length and 1 mm in width. Numbers — Two to six on the petiole and base of leaf blade. Type — Reniform. Color — RHS Brown Group 200C.

*Leaf stipules.*—Size — Medium-long for the variety. Length — Approximately 12 to 19 mm. Color — Green (RHS Yellow Green Group 144B) when young. The stipules are considered to be early deciduous.

*Ratio of wood (leaf) buds to flowering buds.*—1–2 flower buds per leaf bud.

Flowers:

*Flower buds.*—General — The floral buds are considered to be medium to medium large in size, conic in form, and slightly appressed relative to the bearing shoot. The buds are considered hardy under typical central San Joaquin Valley, Calif. and south central Texas climatic conditions. Bud length 4.3 mm. Bud width 3.3 mm. Color 178A (Greyed Red Group) and 166A (Greyed Orange Group).

*Blooming type.*—Considered early in relation to other peach cultivars commonly growing in the central San Joaquin Valley. The date of full bloom was Feb. 18, 2000 in central San Joaquin Valley, and Feb. 23, 2000 in central Texas, which is about 6–8 days after 'Flordaking' (not patented) (Andrews et al. 1979, *HortScience* 14:81–82) and 4 days before 'Texstar' (not patented) (Byrne and Kamas, 1984, *HortScience* 19:453–454).

*Flower type.*—Small, non-showy.

*Flower size.*—Flower diameter at full bloom is approximately 31 to 35 millimeters.

*Bloom quantity.*—Considered abundant.

*Flower bud frequency.*—Normally 1 to 2 appear per node.

*Petal size.*—General — Considered small for the species. Length — Approximately 12 millimeters. Width — Approximately 8 to 10 millimeters.

*Petal form.*—Broadly ovate.

*Petal count.*—Nearly always 5.

*Petal color.*—The petals are red purple. The color shifts from a RHS Red Purple Group 68D at the base of the petal to a RHS Red Purple Group 64D at the tip.

*Petal margins.*—Generally considered variable, from nearly smooth, to undulate and ruffled, especially apically.

*Petal apex.*—General — The petal apices appear slightly domed.

*Flower pedicel.*—Length — Considered medium-short, and having an average length of approximately 2 to 3 millimeters. Color — Medium Green (RHS Yellow-Green Group 143C).

*Calyx.*—Surface Texture — Generally glabrous. Color — A reddish purple (RHS Red Purple Group 59A).

*Sepals.*—Surface Texture — The surface has a short, fine, wooly and and a gray colored texture. Size — Sepal length 8.1 mm. Sepal width 4.0 mm. Color — A grey-purple (RHS Greyed Purple Group 185A) with green (RHS Green Group — 138B).

*Anthers.*—General — Anther length 1.6 mm. Anther width 1.1 mm. Color — Young anthers are yellow-orange (RHS Yellow Orange Group 16B) with a red-purple edge (RHS Red Purple Group 60B). As the anther age, they change color to a greyed-orange (RHS Greyed-Orange Group 163A) with a black edge.

*Pollen production.*—Pollen is yellow (RHS Yellow Orange Group 19B) and abundant.

*Filaments.*—Size — Average 12 millimeters. The filaments are generally slightly shorter than the pistil. Color — Young filaments are off-white (RHS White Group 155C) which change to a very dark pink (RHS Red Purple Group 59B) color with age.

*Pistil.*—General — Relatively short in length, and slightly longer than the anther height. Length — Approximately 13 millimeters, including the ovary. Color — Considered a green-yellow (RHS Green Yellow Group 1 C) when young and becoming slightly more yellowish (RHS Yellow Group 2C) with advancing senescence. Surface Texture — The variety has slender pubescent pistil.

Fruit:

*Maturity when described.*—The present variety of fruit is described, as it would be found in its in its firm ripe condition at full commercial maturity. Under the ecological conditions prevailing in the San Joaquin Valley of Central California, the date of the first picking was Jun. 23, 2000, and the date of the last picking was Jul. 3, 2000. In south central Texas, the present variety began ripening on the $25^{th}$ of May and finished about the 7th of June.

*Size.*—General — Medium large for the season and considered relatively uniform.

*Average fruit weight.*—120 grams when thinned to about one fruit per 20 centimeters of fruiting wood on a third leaf tree, and varies with tree age, soil type, climatic conditions, and cultural practices.

*Average suture diameter.*—Approximately 67 to 82 millimeters.

*Average axial diameter.*—Approximately 67 to 75 millimeters.

*Fruit form.*—Round to ovate in its lateral aspect. The fruit is generally uniform in symmetry when viewed from the apical aspect.

*Fruit suture.*—General — The suture appears as a thin line that extends from the base to the apex. No apparent callusing or stitching exists along the suture line. The suture may protrude slightly. Color — The suture normally is the same color as the underlying blush (RHS Orange Red Group 34C to RHS Red Group 46A).

*Ventral surface.*—Form — Considered uniform.

*Stem cavity.*—Width — Approximately 4 millimeters. Length — Approximately 11 millimeters. Depth — Approximately 5 millimeters. Form — Considered narrowly oval.

*Fruit base.*—General — Considered truncate in form, and uniform.

*Fruit apex.*—General — More prominent in a lower chill, warmer spring climate. In this characteristic, it is similar to the varieties 'TexRoyal' (not patented) (Byrne and Bacon, 1991, *HortScience* 26:1338–1340), and 'Juneprince' (not patented) (Okie and Reilly, 1987, *HortScience* 22:325–326) and much better than the varieties 'Texstar' (not patented) (Byrne and Kamas, 1984, *HortScience* 19:453–454) and 'RioGrande' (U.S. Plant Pat. No. 2,888). (ASHS, 1997, The Brooks and Olmo Register of Fruit and Nut Varieties) 'TexPrince' develops less elongate fruit with less pronounced tips under lower chill conditions as compared to both 'Texstar' (not patented) and 'RioGrande' (U.S. Plant Pat. No. 2,888).

*Fruit skin.*—Considered medium to average in thickness. Surface Texture — The variety has very light, short pubescence. Skin Acidity — Considered neutral. Tenacious to Flesh — Yes at commercial maturity. Tendency to Crack — No cracking has been observed either in Texas or California.

*Skin color.*—Generally — Variable, with approximately 60% to 80% of the fruit surface covered with an attractive red blush.

*Blush color.*—This red blush ranges from RHS Orange Red Group 34C to RHS Red Group 46A with many degrees of shading and blending occurring between these colorations.

*Skin ground color.*—This is generally present in variable percentages covering approximately 20% to 40% of the fruit's surface. The skin ground is yellow ranging from a RHS Yellow Orange Group color of 20B to 22A.

*Flesh color.*—General — Considered variable from a yellow/orange (RHS Yellow Orange Group 15C to 20C) with some red streaks and flecking from the orange-Red Group 34A and from the Red Group 42A, 42B, and 45.

*Flesh texture.*—Generally — The flesh is considered firm and fine at commercial maturity.

*Ripening.*—The fruit of the present variety ripens evenly.

*Flavor.*—Considered sweet and a rich, slightly acidic flavor. The soluble solids ranged from 11 to 14 degree brix.

*Aroma.*—Pleasant and reasonably abundant.

*Eating.*—Considered very good to excellent, particularly for an early mid season ripening variety.

Stone:

*Attachment.*—Generally — Freestone at commercial maturity.

*Stone size.*—Generally — Considered medium relative to the ratio of stone to fruit size. Length — Approximately 32 to 34 millimeters. Width — Approximately 20 to 21 millimeters. Thickness — Approximately 17 to 19 millimeters.

*Stone form.*—General — The stone is considered ovate although somewhat variable.

*Base angle.*—The base angle of the stone is variable, but most frequently is considered medium (70–79 degrees).

*Apex.*—Shape — The stone apex is raised and has an acute tip.

*Hilum.*—Considered medium size. It has an oval shape that ranges from 4–5 mm in length and 2–3 mm in width.

*Stone surface.*—Surface Texture — Generally considered medium to medium-smooth in roughness and exhibits substantial pitting laterally including chains of pits forming grooves.

*Dorsal edge.*—Shape — Medium broad with deep lines and a medium sized ridge.

*Stone color.*—The color of the dry stone ranges in the RHS Greyed Orange Group from 173A to 174C.

*Kernel.*—The kernel fills the inner cavity of the endocarp upon harvest but shrivels when dried. The dried kernel measures approximately 2–3 mm in thickness, 15 mm in length, and 6–8 mm in width. The predominant colors of the dried kernels are the RHS Greyed Orange Group colors of 164A and 165B.

*Tendency to split.*—Not observed.

*Use.*—The subject variety, 'TexPrince', is considered to be a peach tree of early midseason maturity, and which produces fruit that are firm, attractively colored, and useful for both local and long distance shipping. This fruit is useful for the fresh eating market.

*Keeping quality.*—Good.

*Resistance to insects and disease.*—No susceptibilities were noted. It was judged as moderately resistant to bacterial leaf spot (*Xanthomonas campestris* pv. *pruni* (Smith) Dye) as is 'Flordaking' (not patented) in the field plots in College Station.

*Shipping quality.*—Average.

Although the new variety of peach tree possesses the described characteristics when grown under the ecological conditions prevailing near Fowler, Calif., in the central part of the San Joaquin Valley of California or near College Station or Yoakum, Tex., it will be understood that variations of the usual magnitude and characteristics incident to the changes in growing conditions, fertilization, pruning, and pest control are to be expected. It should also be realized by those skilled in the art that such equivalent constructions do not depart from the spirit and scope of the invention as set forth in the appended claim.

What is claimed is:

1. A new and distinct peach tree, as illustrated and described herein.

* * * * *